US010760108B2

(12) United States Patent
Lee et al.

(10) Patent No.: US 10,760,108 B2
(45) Date of Patent: Sep. 1, 2020

(54) MODIFIED RNA POLYMERASE SIGMA FACTOR 70 POLYPEPTIDE

(71) Applicant: CJ CHEILJEDANG CORPORATION, Seoul (KR)

(72) Inventors: Ji Sun Lee, Incheon (KR); Kwang Ho Lee, Daejeon (KR); Hyo Jin Kim, Seoul (KR); Keun Chul Lee, Gyeonggi-do (KR); Young Bin Hwang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/117,437

(22) PCT Filed: Sep. 4, 2015

(86) PCT No.: PCT/KR2015/009381
§ 371 (c)(1),
(2) Date: Aug. 8, 2016

(87) PCT Pub. No.: WO2016/036209
PCT Pub. Date: Mar. 10, 2016

(65) Prior Publication Data
US 2016/0369310 A1    Dec. 22, 2016

(30) Foreign Application Priority Data

Sep. 5, 2014  (KR) .................... 10-2014-0119138
Sep. 4, 2015  (KR) .................... 10-2015-0125440

(51) Int. Cl.
*C12P 13/08*    (2006.01)
*C07K 14/245*   (2006.01)
*C12N 1/21*     (2006.01)
*C12N 9/12*     (2006.01)

(52) U.S. Cl.
CPC ............ *C12P 13/08* (2013.01); *C07K 14/245* (2013.01); *C12N 9/12* (2013.01)

(58) Field of Classification Search
None
See application file for complete search history.

(56) References Cited

U.S. PATENT DOCUMENTS 8,735,132 B2    5/2014   Santos et al.
2011/0151496 A1 * 6/2011  Stephanopoulos .. C12N 9/0071
                                              435/25
2011/0300588 A1 12/2011   Santos et al.

FOREIGN PATENT DOCUMENTS

KR    10-0608085 B1    7/2006
KR    10-2014-0102393 A  8/2014
WO    WO-03054179 A1 *  7/2003  ............. C07K 14/34

OTHER PUBLICATIONS

UniProt Database Accession No. P0A2E4, Jul. 2013, 2 pages (Year: 2013).*
Landini et al., J. Biol. Chem. 273:13307-13312, 1998 (Year: 1998).*
UniProt Database Accession No. P00579, Jul. 2013, 6 pages (Year: 2013).*
Airaksinen et al., Nucleic Acids Res. 26:576-581, 1998 (Year: 1998).*
Schultz et al., Proteins Structure and Function, pp. 521-528, Plenum Press, New York, 1987 (Year: 1987).*
Landini et al., J. Bacteriol. 181:1524-1529, 1999 (Year: 1999).*
Johnson et al., FEMS Microbiol. Lett. 228:193-201, 2003 (Year: 2003).*
Shi et al., "Metal binding properties of single amino acid deletion mutants of zinc finger peptides: studies using cobalt(II) as a spectroscopic probe", Biophys. J. 64:749753, 1993 (Year: 1993).*
Vingadassalom et al., "An unusual primary sigma factor in the Bacteroidetes phylum", Mol. Microbiol. 56:888-902, 2005 (Year: 2005 ).*
Zafar et al., J. Mol. Biol. 401:13-32, 2010 (Year: 2010).*
Bonocora et al., J. Biol. Chem. 286:9290-39296, 2011 (Year: 2011).*
GenPept Database Accession No. WP_117539431, Sep. 2018, 1 page (Year: 2018).*
UniProt Database Accession No. Z5XVC5, Jun. 2014, 1 page (Year: 2014).*
UniProt Database Accession No. A0A378FW19, Nov. 2018, 1 page (Year: 2018).*
Tripathi et al., "Bacterial Sigma Factors as Targets for Engineered or Synthetic Transcriptional Control", Front. Bioeng. Biotechnol. 2:33, Sep. 3, 2014, 7 pages (Year: 2014).*
Alper et al., "Global transcription machinery engineering: A new approach for improving cellular phenotype," Metabolic Engineering 9: 258-267, 2007.
Fenton et al., "*Escherichia coli* promoter opening and—10 recognition: mutational analysis of σ70," The EMBO Journal 19(5): 1130-1137, 2000.
Gruber et al., "Multiple Sigma Subunits and the Partitioning of Bacterial Transcription Space," Annu. Rev. Microbiol. 57:441-66, 2003.
Jishage et al., "Regulation of RNA Polymerase Sigma Subunit Synthesis in *Escherichia coli*: Intracellular Levels of Four Species of Sigma Subunit under Various Growth Conditions," Journal of Bacteriology 178(18): 5447-5451, Sep. 1996.
Lacour et al., "Substitutions in Region 2.4 of sigma70 Allow Recognition of the sigmaS-Dependent aidB Promoter," The Journal of Biological Chemistry 279(53): 55255-55261, Dec. 31, 2004.
NCBI Reference Sequence: WP_000437376.1 "RNA polymerase sigma factor RpoD [*Escherichia coli*]," May 15, 2013, one page.
Callaci et al., "Conformational Changes of *Escherichia coli* RNA Polymerase sigma70 Factor Induced by Binding to the Core Enzyme," The Journal of Biological Chemistry 273(49): 32995-33001, Dec. 4, 1998.

* cited by examiner

*Primary Examiner* — David Steadman
(74) *Attorney, Agent, or Firm* — Cooley LLP

(57) ABSTRACT

The present invention relates to a novel variant RNA polymerase sigma factor 70 ($\pi^{70}$) polypeptide, a polynucleotide encoding the same, a microorganism containing the polypeptide, and a method for producing L-threonine by using the microorganism.

9 Claims, No Drawings
Specification includes a Sequence Listing.

SEQUENCE LISTING

<160> NUMBER OF SEQ ID NOS: 37

<210> SEQ ID NO 1
<211> LENGTH: 31
<212> TYPE: DNA
<213> ORGANISM: Artificial Sequence
<220> FEATURE:
<223> OTHER INFORMATION: Primer

<400> SEQUENCE: 1
tactcaagct tcggcttaag tgccgaagag c        31

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
agggcgaatt cctgatccgg cctaccgatt a        31

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gacggatcca ccaggttgcg ta        22

```
<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
aacctggtgg atccgtcagg cgatc                                           25

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
cgagaagctt agcttttcat tctgactgca                                      30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cgagaagctt attgagataa tgaatagatt                                      30

<210> SEQ ID NO 7
<211> LENGTH: 1842
<212> TYPE: DNA
<213> ORGANISM: Escherichia coli

<400> SEQUENCE: 7
atggagcaaa acccgcagtc acagctgaaa cttcttgtca cccgtggtaa ggagcaaggc      60
tatctgacct atgccgaggt caatgaccat ctgccggaag atatcgtcga ttcagatcag     120
atcgaagaca tcatccaaat gatcaacgac atgggcattc aggtgatgga agaagcaccg     180
gatgccgatg atctgatgct ggctgaaaac accgcggacg aagatgctgc cgaagccgcc     240
gcgcaggtgc tttccagcgt ggaatctgaa atcgggcgca cgactgaccc ggtacgcatg     300
tacatgcgtg aaatgggcac cgttgaactg ttgacccgcg aaggcgaaat tgacatcgct     360
aagcgtattg aagacgggat caaccaggtt caatgctccg ttgctgaata tccggaagcg     420
atcacctatc tgctggaaca gtacgatcgt gttgaagcag aagaagcgcg tctgtccgat     480
ctgatcaccg gctttgttga cccgaacgca gaagaagatc tggcacctac cgccactcac     540
gtcggttctg agctttccca ggaagatctg gacgatgacg aagatgaaga cgaagaagat     600
ggcgatgacg acagcgccga tgatgacaac agcatcgacc cggaactggc tcgcgaaaaa     660
tttgcggaac tacgcgctca gtacgttgta acgcgtgaca ccatcaaagc gaaaggtcgc     720
agtcacgcta ccgctcagga agagatcctg aaactgtctg aagtattcaa acagttccgc     780
ctggtgccga agcagtttga ctacctggtc aacagcatgc gcgtcatgat ggaccgcgtt     840
cgtacgcaag aacgtctgat catgaagctc tgcgttgagc agtgcaaaat gccgaagaaa     900
aacttcatta ccctgtttac cggcaacgaa accagcgata cctggttcaa cgcggcaatt     960
gcgatgaaca gccgtggtc ggaaaaactg cacgatgtct ctgaagaagt gcatcgcgcc    1020
ctgcaaaaac tgcagcagat tgaagaagaa accggcctga ccatcgagca ggttaaagat    1080
```

-continued

```
atcaaccgtc gtatgtccat cggtgaagcg aaagcccgcc gtgcgaagaa agagatggtt    1140
gaagcgaact tacgtctggt tatttctatc gctaagaaat acaccaaccg tggcttgcag    1200
ttccttgacc tgattcagga aggcaacatc ggtctgatga aagcggttga taaattcgaa    1260
taccgccgtg gttacaagtt ctccacctac gcaacctggt ggatccgtca ggcgatcacc    1320
cgctctatcg cggatcaggc gcgcaccatc cgtattccgg tgcatatgat tgagaccatc    1380
aacaagctca accgtatttc tcgccagatg ctgcaagaga tgggccgtga accgacgccg    1440
gaagaactgg ctgaacgtat gctgatgccg gaagacaaga tccgcaaagt gctgaagatc    1500
gccaaagagc caatctccat ggaaacgccg atcggtgatg atgaagattc gcatctgggg    1560
gatttcatcg aggataccac cctcgagctg ccgctggatt ctgcgaccac cgaaagcctg    1620
cgtgcggcaa cgcacgacgt gctggctggc ctgaccgcgc gtgaagcaaa agttctgcgt    1680
atgcgtttcg gtatcgatat gaacaccgac tacacgctgg aagaagtggg taaacagttc    1740
gacgttaccc gcgaacgtat ccgtcagatc gaagcgaagg cgctgcgcaa actgcgtcac    1800
ccgagccgtt ctgaagtgct gcgtagcttc ctggacgatt aa                       1842
```

<210> SEQ ID NO 8
<211> LENGTH: 613
<212> TYPE: PRT
<213> ORGANISM: Escherichia coli

<400> SEQUENCE: 8

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240
```

Ser His Ala Thr Ala Gln Glu Glu Ile Leu Lys Leu Ser Glu Val Phe
            245                 250                 255

Lys Gln Phe Arg Leu Val Pro Lys Gln Phe Asp Tyr Leu Val Asn Ser
        260                 265                 270

Met Arg Val Met Met Asp Arg Val Arg Thr Gln Glu Arg Leu Ile Met
    275                 280                 285

Lys Leu Cys Val Glu Gln Cys Lys Met Pro Lys Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
            325                 330                 335

Val His Arg Ala Leu Gln Lys Leu Gln Gln Ile Glu Glu Thr Gly
        340                 345                 350

Leu Thr Ile Glu Gln Val Lys Asp Ile Asn Arg Arg Met Ser Ile Gly
    355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
            405                 410                 415

Asp Lys Phe Glu Tyr Arg Arg Gly Tyr Lys Phe Ser Thr Tyr Ala Thr
        420                 425                 430

Trp Trp Ile Arg Gln Ala Ile Thr Arg Ser Ile Ala Asp Gln Ala Arg
    435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
            485                 490                 495

Val Leu Lys Ile Ala Lys Glu Pro Ile Ser Met Glu Thr Pro Ile Gly
        500                 505                 510

Asp Asp Glu Asp Ser His Leu Gly Asp Phe Ile Glu Asp Thr Thr Leu
    515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
            565                 570                 575

Gly Lys Gln Phe Asp Val Thr Arg Glu Arg Ile Arg Gln Ile Glu Ala
        580                 585                 590

Lys Ala Leu Arg Lys Leu Arg His Pro Ser Arg Ser Glu Val Leu Arg
    595                 600                 605

Ser Phe Leu Asp Asp
    610

<210> SEQ ID NO 9
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 9

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
        50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
```

```
                      405                 410                 415
Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
            450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
            530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Arg Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
            595                 600                 605

Ser Phe Leu Gly Asp
            610

<210> SEQ ID NO 10
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 10

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Glu Ala Arg Leu Ser Asp
```

-continued

```
        145                 150                 155                 160
Leu Ile Thr Gly Phe Val Asp Pro Asn Ala Glu Glu Asp Leu Ala Pro
                    165                 170                 175
Thr Ala Thr His Val Gly Ser Glu Leu Ser Gln Glu Asp Leu Asp Asp
                    180                 185                 190
Asp Glu Asp Glu Asp Glu Asp Gly Asp Asp Ser Ala Asp Asp
                195                 200                 205
Asp Asn Ser Ile Asp Pro Glu Leu Ala Arg Glu Lys Phe Ala Glu Leu
        210                 215                 220
Arg Ala Gln Tyr Val Val Thr Arg Asp Thr Ile Lys Ala Lys Gly Arg
225                 230                 235                 240
Ser His Ala Thr Ala Gln Glu Ile Leu Lys Leu Ser Glu Val Phe
                    245                 250                 255
Lys Gln Phe Arg Leu Val Pro Lys Gln Phe Asp Tyr Leu Val Asn Ser
                260                 265                 270
Met Arg Val Met Met Asp Arg Val Arg Thr Gln Glu Arg Leu Ile Met
                275                 280                 285
Lys Leu Cys Val Glu Gln Cys Lys Met Pro Lys Lys Asn Phe Ile Thr
        290                 295                 300
Leu Phe Thr Gly Asn Glu Thr Ser Asp Thr Trp Phe Asn Ala Ala Ile
305                 310                 315                 320
Ala Met Asn Lys Pro Trp Ser Glu Lys Leu His Asp Val Ser Glu Glu
                325                 330                 335
Val His Arg Ala Leu Gln Lys Leu Gln Gln Ile Glu Glu Thr Gly
                340                 345                 350
Leu Thr Ile Glu Gln Val Lys Asp Ile Asn Arg Arg Met Ser Ile Gly
            355                 360                 365
Glu Ala Lys Ala Arg Arg Ala Lys Lys Glu Met Val Glu Ala Asn Leu
                370                 375                 380
Arg Leu Val Ile Ser Ile Ala Lys Lys Tyr Thr Asn Arg Gly Leu Gln
385                 390                 395                 400
Phe Leu Asp Leu Ile Gln Glu Gly Asn Ile Gly Leu Met Lys Ala Val
                    405                 410                 415
Asp Lys Phe Glu Tyr Arg Arg Gly Tyr Lys Phe Ser Thr Tyr Ala Thr
                420                 425                 430
Trp Trp Ile Arg Gln Ala Ile Thr Arg Ser Ile Ala Asp Gln Ala Arg
                435                 440                 445
Thr Ile Arg Ile Pro Val His Met Ile Glu Thr Ile Asn Lys Leu Asn
        450                 455                 460
Arg Ile Ser Arg Gln Met Leu Gln Glu Met Gly Arg Glu Pro Thr Pro
465                 470                 475                 480
Glu Glu Leu Ala Glu Arg Met Leu Met Pro Glu Asp Lys Ile Arg Lys
                    485                 490                 495
Val Leu Lys Ile Ala Lys Glu Pro Ile Ser Met Glu Thr Pro Ile Gly
                500                 505                 510
Asp Asp Glu Asp Ser His Leu Gly Asp Phe Ile Glu Asp Thr Thr Leu
                515                 520                 525
Glu Leu Pro Leu Asp Ser Ala Thr Thr Glu Ser Leu Arg Ala Ala Thr
                530                 535                 540
His Asp Val Leu Ala Gly Leu Thr Ala Arg Glu Ala Lys Val Leu Arg
545                 550                 555                 560
Met Arg Phe Gly Ile Asp Met Asn Thr Asp Tyr Thr Leu Glu Glu Val
                    565                 570                 575
```

-continued

```
Gly Lys Arg Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Tyr Asp
    610

<210> SEQ ID NO 11
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 11

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Asn Phe Ile Thr
    290                 295                 300

Leu Phe Thr Gly Asn Glu Thr Ser Asp Thr Trp Phe Asn Ala Ala Ile
305                 310                 315                 320
```

Ala Met Asn Lys Pro Trp Ser Glu Lys Leu His Asp Val Ser Glu
            325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
            405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
            450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
            485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
            530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
            565                 570                 575

Gly Lys Leu Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
            595                 600                 605

Ser Phe Leu Thr Asp
    610

<210> SEQ ID NO 12
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 12

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Gln Met Ile
        35                  40                  45

Asn Asp Met Gly Ile Gln Val Met Glu Glu Ala Pro Asp Ala Asp Asp
    50                  55                  60

```
Leu Met Leu Ala Glu Asn Thr Ala Asp Glu Asp Ala Ala Glu Ala Ala
 65                  70                  75                  80

Ala Gln Val Leu Ser Ser Val Glu Ser Glu Ile Gly Arg Thr Thr Asp
                 85                  90                  95

Pro Val Arg Met Tyr Met Arg Glu Met Gly Thr Val Glu Leu Leu Thr
                100                 105                 110

Arg Glu Gly Glu Ile Asp Ile Ala Lys Arg Ile Glu Asp Gly Ile Asn
            115                 120                 125

Gln Val Gln Cys Ser Val Ala Glu Tyr Pro Glu Ala Ile Thr Tyr Leu
        130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
                180                 185                 190

Asp Glu Asp Glu Asp Glu Asp Gly Asp Asp Asp Ser Ala Asp Asp
            195                 200                 205

Asp Asn Ser Ile Asp Pro Glu Leu Ala Arg Glu Lys Phe Ala Glu Leu
210                 215                 220

Arg Ala Gln Tyr Val Val Thr Arg Asp Thr Ile Lys Ala Lys Gly Arg
225                 230                 235                 240

Ser His Ala Thr Ala Gln Glu Ile Leu Lys Leu Ser Glu Val Phe
                245                 250                 255

Lys Gln Phe Arg Leu Val Pro Lys Gln Phe Asp Tyr Leu Val Asn Ser
                260                 265                 270

Met Arg Val Met Met Asp Arg Val Arg Thr Gln Glu Arg Leu Ile Met
            275                 280                 285

Lys Leu Cys Val Glu Gln Cys Lys Met Pro Lys Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
        370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
        450                 455                 460

Arg Ile Ser Arg Gln Met Leu Gln Glu Met Gly Arg Glu Pro Thr Pro
465                 470                 475                 480
```

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
        500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
        530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Arg Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
                595                 600                 605

Ser Phe Leu Asn Asp
        610

<210> SEQ ID NO 13
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 13

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
        50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
            245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
            275                 280                 285

Lys Leu Cys Val Glu Gln Cys Lys Met Pro Lys Lys Asn Phe Ile Thr
            290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
            325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
            405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
            450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
            485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
            530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
            565                 570                 575

Gly Lys Thr Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
            595                 600                 605

Ser Phe Leu Gly Asp
    610

<210> SEQ ID NO 14
<211> LENGTH: 613
<212> TYPE: PRT

<213> ORGANISM: Artificial Sequence
<220> FEATURE:
<223> OTHER INFORMATION: Modified rpoD variant

<400> SEQUENCE: 14

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
```

```
385                 390                 395                 400
    Phe Leu Asp Leu Ile Gln Glu Gly Asn Ile Gly Leu Met Lys Ala Val
                    405                 410                 415

Asp Lys Phe Glu Tyr Arg Arg Gly Tyr Lys Phe Ser Thr Tyr Ala Thr
                    420                 425                 430

Trp Trp Ile Arg Gln Ala Ile Thr Arg Ser Ile Ala Asp Gln Ala Arg
                    435                 440                 445

Thr Ile Arg Ile Pro Val His Met Ile Glu Thr Ile Asn Lys Leu Asn
                    450                 455                 460

Arg Ile Ser Arg Gln Met Leu Gln Glu Met Gly Arg Glu Pro Thr Pro
    465                 470                 475                 480

Glu Glu Leu Ala Glu Arg Met Leu Met Pro Glu Asp Lys Ile Arg Lys
                    485                 490                 495

Val Leu Lys Ile Ala Lys Glu Pro Ile Ser Met Glu Thr Pro Ile Gly
                    500                 505                 510

Asp Asp Glu Asp Ser His Leu Gly Asp Phe Ile Glu Asp Thr Thr Leu
                    515                 520                 525

Glu Leu Pro Leu Asp Ser Ala Thr Thr Glu Ser Leu Arg Ala Ala Thr
                    530                 535                 540

His Asp Val Leu Ala Gly Leu Thr Ala Arg Glu Ala Lys Val Leu Arg
    545                 550                 555                 560

Met Arg Phe Gly Ile Asp Met Asn Thr Asp Tyr Thr Leu Glu Glu Val
                    565                 570                 575

Gly Lys Arg Phe Asp Val Thr Arg Glu Arg Ile Arg Gln Ile Glu Ala
                    580                 585                 590

Lys Ala Leu Arg Lys Leu Arg His Pro Ser Arg Ser Glu Val Leu Arg
                    595                 600                 605

Ser Phe Leu Phe Asp
                    610

<210> SEQ ID NO 15
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 15

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
                35                  40                  45

Asn Asp Met Gly Ile Gln Val Met Glu Glu Ala Pro Asp Ala Asp Asp
                50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
                100                 105                 110

Arg Glu Gly Glu Ile Asp Ile Ala Lys Arg Ile Glu Asp Gly Ile Asn
                115                 120                 125

Gln Val Gln Cys Ser Val Ala Glu Tyr Pro Glu Ala Ile Thr Tyr Leu
```

-continued

```
            130                 135                 140
Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
                180                 185                 190

Asp Glu Asp Glu Asp Glu Glu Asp Gly Asp Asp Ser Ala Asp Asp
                195                 200                 205

Asp Asn Ser Ile Asp Pro Glu Leu Ala Arg Glu Lys Phe Ala Glu Leu
210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
                260                 265                 270

Met Arg Val Met Met Asp Arg Val Arg Thr Gln Glu Arg Leu Ile Met
                275                 280                 285

Lys Leu Cys Val Glu Gln Cys Lys Met Pro Lys Lys Asn Phe Ile Thr
                290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
                340                 345                 350

Leu Thr Ile Glu Gln Val Lys Asp Ile Asn Arg Arg Met Ser Ile Gly
                355                 360                 365

Glu Ala Lys Ala Arg Arg Ala Lys Lys Glu Met Val Glu Ala Asn Leu
                370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
                435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
                500                 505                 510

Asp Asp Glu Asp Ser His Leu Gly Asp Phe Ile Glu Asp Thr Thr Leu
                515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560
```

```
Met Arg Phe Gly Ile Asp Met Asn Thr Asp Tyr Thr Leu Glu Glu Val
                565                 570                 575
Gly Lys Ile Phe Asp Val Thr Arg Glu Arg Ile Arg Gln Ile Glu Ala
                580                 585                 590
Lys Ala Leu Arg Lys Leu Arg His Pro Ser Arg Ser Glu Val Leu Arg
                595                 600                 605
Ser Phe Leu Lys Asp
                610

<210> SEQ ID NO 16
<211> LENGTH: 611
<212> TYPE: PRT
<213> ORGANISM: Artificial Sequence
<220> FEATURE:
<223> OTHER INFORMATION: Modified rpoD variant

<400> SEQUENCE: 16

Met Glu Gln Asn Pro Gln Ser Gln Leu Lys Leu Leu Val Thr Arg Gly
1               5                   10                  15
Lys Glu Gln Gly Tyr Leu Thr Tyr Ala Glu Val Asn Asp His Leu Pro
                20                  25                  30
Glu Asp Ile Val Asp Ser Asp Gln Ile Glu Asp Ile Ile Gln Met Ile
                35                  40                  45
Asn Asp Met Gly Ile Gln Val Met Glu Glu Ala Pro Asp Ala Asp Asp
        50                  55                  60
Leu Met Leu Ala Glu Asn Thr Ala Asp Glu Asp Ala Ala Glu Ala Ala
65                  70                  75                  80
Ala Gln Val Leu Ser Ser Val Glu Ser Glu Ile Gly Arg Thr Thr Asp
                85                  90                  95
Pro Val Arg Met Tyr Met Arg Glu Met Gly Thr Val Glu Leu Leu Thr
                100                 105                 110
Arg Glu Gly Glu Ile Asp Ile Ala Lys Arg Ile Glu Asp Gly Ile Asn
                115                 120                 125
Gln Val Gln Cys Ser Val Ala Glu Tyr Pro Glu Ala Ile Thr Tyr Leu
        130                 135                 140
Leu Glu Gln Tyr Asp Arg Val Glu Ala Glu Ala Arg Leu Ser Asp
145                 150                 155                 160
Leu Ile Thr Gly Phe Val Asp Pro Asn Ala Glu Glu Asp Leu Ala Pro
                165                 170                 175
Thr Ala Thr His Val Gly Ser Glu Leu Ser Gln Glu Asp Leu Asp Asp
                180                 185                 190
Asp Glu Asp Glu Asp Glu Glu Asp Gly Asp Asp Ser Ala Asp Asp
        195                 200                 205
Asp Asn Ser Ile Asp Pro Glu Leu Ala Arg Glu Lys Phe Ala Glu Leu
        210                 215                 220
Arg Ala Gln Tyr Val Val Thr Arg Asp Thr Ile Lys Ala Lys Gly Arg
225                 230                 235                 240
Ser His Ala Thr Ala Gln Glu Glu Ile Leu Lys Leu Ser Glu Val Phe
                245                 250                 255
Lys Gln Phe Arg Leu Val Pro Lys Gln Phe Asp Tyr Leu Val Asn Ser
                260                 265                 270
Met Arg Val Met Met Asp Arg Val Arg Thr Gln Glu Arg Leu Ile Met
                275                 280                 285
Lys Leu Cys Val Glu Gln Cys Lys Met Pro Lys Lys Asn Phe Ile Thr
        290                 295                 300
```

```
Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
            325                 330                 335

Val His Arg Ala Leu Gln Lys Leu Gln Gln Ile Glu Glu Thr Gly
        340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
        435                 440                 445

Thr Ile Arg Ile Pro Val His Met Ile Glu Thr Ile Asn Lys Leu Asn
450                 455                 460

Arg Ile Ser Arg Gln Met Leu Gln Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Leu Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu
    610

<210> SEQ ID NO 17
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 17

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45
```

```
Asn Asp Met Gly Ile Gln Val Met Glu Glu Ala Pro Asp Ala Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                    85                  90                  95

Pro Val Arg Met Tyr Met Arg Glu Met Gly Thr Val Glu Leu Leu Thr
                100                 105                 110

Arg Glu Gly Glu Ile Asp Ile Ala Lys Arg Ile Glu Asp Gly Ile Asn
                115                 120                 125

Gln Val Gln Cys Ser Val Ala Glu Tyr Pro Glu Ala Ile Thr Tyr Leu
            130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
                180                 185                 190

Asp Glu Asp Glu Asp Glu Glu Asp Gly Asp Asp Asp Ser Ala Asp Asp
            195                 200                 205

Asp Asn Ser Ile Asp Pro Glu Leu Ala Arg Glu Lys Phe Ala Glu Leu
        210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
                260                 265                 270

Met Arg Val Met Met Asp Arg Val Arg Thr Gln Glu Arg Leu Ile Met
                275                 280                 285

Lys Leu Cys Val Glu Gln Cys Lys Met Pro Lys Lys Asn Phe Ile Thr
            290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
                340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
        370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
        450                 455                 460
```

```
Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
        530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gly Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Ser Asp
    610

<210> SEQ ID NO 18
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 18

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205
```

```
Asp Asn Ser Ile Asp Pro Glu Leu Ala Arg Glu Lys Phe Ala Glu Leu
210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
                260                 265                 270

Met Arg Val Met Met Asp Arg Arg Thr Gln Glu Arg Leu Ile Met
            275                 280                 285

Lys Leu Cys Val Glu Gln Cys Lys Met Pro Lys Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
            450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
                500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Ala Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
                595                 600                 605

Ser Phe Leu Phe Asp
            610
```

-continued

```
<210> SEQ ID NO 19
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 19

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
```

```
                370                 375                 380
Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
                500                 505                 510

Asp Asp Glu Asp Ser His Leu Gly Asp Phe Ile Glu Asp Thr Thr Leu
                515                 520                 525

Glu Leu Pro Leu Asp Ser Ala Thr Thr Glu Ser Leu Arg Ala Ala Thr
            530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Pro Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
            595                 600                 605

Ser Phe Leu Arg Asp
    610

<210> SEQ ID NO 20
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 20

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
                100                 105                 110

Arg Glu Gly Glu Ile Asp Ile Ala Lys Arg Ile Glu Asp Gly Ile Asn
```

```
                    115                 120                 125
Gln Val Gln Cys Ser Val Ala Glu Tyr Pro Glu Ala Ile Thr Tyr Leu
            130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                    165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
            195                 200                 205

Asp Asn Ser Ile Asp Pro Glu Leu Ala Arg Glu Lys Phe Ala Glu Leu
        210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                    245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
            275                 280                 285

Lys Leu Cys Val Glu Gln Cys Lys Met Pro Lys Lys Asn Phe Ile Thr
        290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                    325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
        370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                    405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
        450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                    485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
        530                 535                 540
```

```
His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Ser Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu His Asp
    610

<210> SEQ ID NO 21
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 21

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285
```

-continued

```
Lys Leu Cys Val Glu Gln Cys Lys Met Pro Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
            325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
            370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Arg Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
            595                 600                 605

Ser Phe Leu His Asp
    610
```

<210> SEQ ID NO 22
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 22

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30
```

```
Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
 50                  55                  60

Leu Met Leu Ala Glu Asn Thr Ala Asp Glu Asp Ala Ala Glu Ala Ala
 65                  70                  75                  80

Ala Gln Val Leu Ser Ser Val Glu Ser Glu Ile Gly Arg Thr Thr Asp
                 85                  90                  95

Pro Val Arg Met Tyr Met Arg Glu Met Gly Thr Val Glu Leu Leu Thr
             100                 105                 110

Arg Glu Gly Glu Ile Asp Ile Ala Lys Arg Ile Glu Asp Gly Ile Asn
             115                 120                 125

Gln Val Gln Cys Ser Val Ala Glu Tyr Pro Glu Ala Ile Thr Tyr Leu
130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Asp Leu Ala Pro
                 165                 170                 175

Thr Ala Thr His Val Gly Ser Glu Leu Ser Gln Glu Asp Leu Asp Asp
             180                 185                 190

Asp Glu Asp Glu Asp Glu Glu Asp Gly Asp Asp Asp Ser Ala Asp Asp
             195                 200                 205

Asp Asn Ser Ile Asp Pro Glu Leu Ala Arg Glu Lys Phe Ala Glu Leu
         210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                 245                 250                 255

Lys Gln Phe Arg Leu Val Pro Lys Gln Phe Asp Tyr Leu Val Asn Ser
             260                 265                 270

Met Arg Val Met Met Asp Arg Val Arg Thr Gln Glu Arg Leu Ile Met
         275                 280                 285

Lys Leu Cys Val Glu Gln Cys Lys Met Pro Lys Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
             325                 330                 335

Val His Arg Ala Leu Gln Lys Leu Gln Gln Ile Glu Glu Glu Thr Gly
             340                 345                 350

Leu Thr Ile Glu Gln Val Lys Asp Ile Asn Arg Arg Met Ser Ile Gly
             355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                 405                 410                 415

Asp Lys Phe Glu Tyr Arg Arg Gly Tyr Lys Phe Ser Thr Tyr Ala Thr
             420                 425                 430

Trp Trp Ile Arg Gln Ala Ile Pro Arg Ser Ile Ala Asp Gln Ala Arg
             435                 440                 445
```

-continued

```
Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Asp Asp
610

<210> SEQ ID NO 23
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 23

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190
```

Asp Glu Asp Glu Asp Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Pro Arg Ser Ile Ala Asp Gln Ala Arg
        435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Asn
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Asp Asp

<210> SEQ ID NO 24
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 24

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
```

```
                    355                 360                 365
Glu Ala Lys Ala Arg Ala Lys Lys Glu Met Val Glu Ala Asn Leu
    370                 375                 380
Arg Leu Val Ile Ser Ile Ala Lys Lys Tyr Thr Asn Arg Gly Leu Gln
385                 390                 395                 400
Phe Leu Asp Leu Ile Gln Glu Gly Asn Ile Gly Leu Met Lys Ala Val
                    405                 410                 415
Asp Lys Phe Glu Tyr Arg Arg Gly Tyr Lys Phe Ser Thr Tyr Ala Thr
                420                 425                 430
Trp Trp Ile Arg Gln Ala Ile Thr Arg Ser Ile Ala Asp Pro Ala Ser
            435                 440                 445
Thr Ile Arg Ile Pro Val His Met Ile Glu Thr Ile Asn Lys Leu Asn
    450                 455                 460
Arg Ser Ser Arg Gln Met Leu Gln Glu Met Gly Arg Glu Pro Thr Pro
465                 470                 475                 480
Glu Glu Leu Ala Glu Arg Met Leu Met Pro Glu Asp Lys Ile Arg Lys
                    485                 490                 495
Val Leu Lys Ile Ala Lys Glu Pro Ile Ser Met Glu Thr Pro Ile Gly
                500                 505                 510
Asp Asp Glu Asp Ser His Leu Gly Asp Phe Ile Glu Asp Thr Pro Leu
            515                 520                 525
Glu Leu Pro Leu Asp Ser Ala Thr Thr Glu Ser Leu Arg Ala Ala Thr
    530                 535                 540
His Asp Val Leu Ala Gly Leu Thr Ala Arg Glu Ala Lys Val Leu Arg
545                 550                 555                 560
Met Arg Phe Gly Ile Asp Val Asn Thr Asp Tyr Thr Leu Glu Glu Val
                    565                 570                 575
Gly Lys Gln Phe Asp Val Thr Arg Glu Arg Ile Arg Gln Ile Glu Ala
                580                 585                 590
Lys Ala Leu Arg Lys Leu Arg His Pro Ser Arg Ser Glu Val Leu Arg
            595                 600                 605
Ser Phe Leu Asp Asp
    610

<210> SEQ ID NO 25
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 25

Met Glu Gln Asn Pro Gln Ser Gln Leu Lys Leu Leu Val Thr Arg Gly
1               5                   10                  15
Lys Glu Gln Gly Tyr Leu Thr Tyr Ala Glu Val Asn Asp His Leu Pro
            20                  25                  30
Glu Asp Ile Val Asp Ser Asp Gln Ile Glu Asp Ile Ile Gln Met Ile
        35                  40                  45
Asn Asp Met Gly Ile Gln Val Met Glu Glu Ala Pro Asp Ala Asp Asp
    50                  55                  60
Leu Met Leu Ala Glu Asn Thr Ala Asp Glu Asp Ala Ala Glu Ala Ala
65                  70                  75                  80
Ala Gln Val Leu Ser Ser Val Glu Ser Glu Ile Gly Arg Thr Thr Asp
                85                  90                  95
Pro Val Arg Met Tyr Met Arg Glu Met Gly Thr Val Glu Leu Leu Thr
```

```
            100                 105                 110
    Arg Glu Gly Glu Ile Asp Ile Ala Lys Arg Ile Glu Asp Gly Ile Asn
                    115                 120                 125

Gln Val Gln Cys Ser Val Ala Glu Tyr Pro Glu Ala Ile Thr Tyr Leu
            130                 135                 140

Leu Glu Gln Tyr Asp Arg Val Glu Ala Glu Ala Arg Leu Ser Asp
    145                 150                 155                 160

Leu Ile Thr Gly Phe Val Asp Pro Asn Ala Glu Glu Asp Leu Ala Pro
                    165                 170                 175

Thr Ala Thr His Val Gly Ser Glu Leu Ser Gln Glu Asp Leu Asp Asp
                    180                 185                 190

Asp Glu Asp Glu Asp Glu Asp Gly Asp Asp Ser Ala Asp Asp
            195                 200                 205

Asp Asn Ser Ile Asp Pro Glu Leu Ala Arg Glu Lys Phe Ala Glu Leu
            210                 215                 220

Arg Ala Gln Tyr Val Val Thr Arg Asp Thr Ile Lys Ala Lys Gly Arg
    225                 230                 235                 240

Ser His Ala Thr Ala Gln Glu Glu Ile Leu Lys Leu Ser Glu Val Phe
                    245                 250                 255

Lys Gln Phe Arg Leu Val Pro Lys Gln Phe Asp Tyr Leu Val Asn Ser
                    260                 265                 270

Met Arg Val Met Met Asp Arg Val Arg Thr Gln Glu Arg Leu Ile Met
                    275                 280                 285

Lys Leu Cys Val Glu Gln Cys Lys Met Pro Lys Lys Asn Phe Ile Thr
            290                 295                 300

Leu Phe Thr Gly Asn Glu Thr Ser Asp Thr Trp Phe Asn Ala Ala Ile
    305                 310                 315                 320

Ala Met Asn Lys Pro Trp Ser Glu Lys Leu His Asp Val Ser Glu Glu
                    325                 330                 335

Val His Arg Ala Leu Gln Lys Leu Gln Gln Ile Glu Glu Thr Gly
                    340                 345                 350

Leu Thr Ile Glu Gln Val Lys Asp Ile Asn Arg Arg Met Ser Ile Gly
                    355                 360                 365

Glu Ala Lys Ala Arg Arg Ala Lys Lys Glu Met Val Glu Ala Asn Leu
            370                 375                 380

Arg Leu Val Ile Ser Ile Ala Lys Lys Tyr Thr Asn Arg Gly Leu Gln
    385                 390                 395                 400

Phe Leu Asp Leu Ile Gln Glu Gly Asn Ile Gly Leu Met Lys Ala Val
                    405                 410                 415

Asp Lys Phe Glu Tyr Arg Arg Gly Tyr Lys Phe Ser Thr Tyr Ala Thr
                    420                 425                 430

Trp Trp Ile Arg Gln Ala Ile Pro Arg Ser Ile Ala Asp Gln Ala Arg
                    435                 440                 445

Thr Ile Arg Ile Pro Val His Met Ile Glu Thr Ile Asn Lys Leu Asn
                    450                 455                 460

Arg Ile Ser Arg Gln Met Leu Gln Glu Met Gly Arg Gly Pro Thr Pro
    465                 470                 475                 480

Glu Glu Leu Ala Glu Arg Met Leu Met Pro Gly Asp Lys Ile Arg Lys
                    485                 490                 495

Val Arg Lys Ile Ala Lys Glu Pro Ile Ser Met Glu Thr Pro Ile Gly
                    500                 505                 510

Asp Asp Glu Asp Ser His Leu Gly Asp Phe Ile Glu Asp Thr Thr Leu
                    515                 520                 525
```

Glu Leu Pro Leu Asp Ser Ala Thr Thr Glu Ser Leu Arg Ala Ala Thr
            530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
            595                 600                 605

Ser Phe Leu Asp Asp
    610

<210> SEQ ID NO 26
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 26

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
            85                  90                  95

Pro Val Arg Met Tyr Met Arg Glu Met Gly Thr Val Glu Leu Leu Thr
        100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
            275                 280                 285

Lys Leu Cys Val Glu Gln Cys Lys Met Pro Lys Lys Asn Phe Ile Thr
        290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Pro Arg Ser Ile Ala Asp Gln Ala Arg
        435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Cys His Pro Ser Arg Ser Glu Val Leu Arg
        595                 600                 605

Ser Phe Leu Asp Asp
    610

<210> SEQ ID NO 27
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 27

Met Glu Gln Asn Pro Gln Ser Gln Leu Lys Leu Leu Val Thr Arg Gly
1               5                   10                  15

```
Lys Glu Gln Gly Tyr Leu Thr Tyr Ala Glu Val Asn Asp His Leu Pro
             20                  25                  30

Glu Asp Ile Val Asp Ser Asp Gln Ile Glu Asp Ile Ile Gln Met Ile
         35                  40                  45

Asn Asp Met Gly Ile Gln Val Met Glu Glu Ala Pro Asp Ala Asp Asp
 50                  55                  60

Leu Met Leu Ala Glu Asn Thr Ala Asp Glu Asp Ala Ala Glu Ala Ala
 65                  70                  75                  80

Ala Gln Val Leu Ser Ser Val Glu Ser Glu Ile Gly Arg Thr Thr Asp
                 85                  90                  95

Pro Val Arg Met Tyr Met Arg Glu Met Gly Thr Val Glu Leu Leu Thr
             100                 105                 110

Arg Glu Gly Glu Ile Asp Ile Ala Lys Arg Ile Glu Asp Gly Ile Asn
         115                 120                 125

Gln Val Gln Cys Ser Val Ala Glu Tyr Pro Glu Ala Ile Thr Tyr Leu
130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                 165                 170                 175

Thr Ala Thr His Val Gly Ser Glu Leu Ser Gln Glu Asp Leu Asp Asp
             180                 185                 190

Asp Glu Asp Glu Asp Glu Glu Asp Gly Asp Asp Ser Ala Asp Asp
         195                 200                 205

Asp Asn Ser Ile Asp Pro Glu Leu Ala Arg Glu Lys Phe Ala Glu Leu
210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
             245                 250                 255

Lys Gln Phe Arg Leu Val Pro Lys Gln Phe Asp Tyr Leu Val Asn Ser
             260                 265                 270

Met Arg Val Met Met Asp Arg Val Arg Thr Gln Glu Arg Leu Ile Met
             275                 280                 285

Lys Leu Cys Val Glu Gln Cys Lys Met Pro Lys Lys Asn Phe Ile Thr
         290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                 325                 330                 335

Val His Arg Ala Leu Gln Lys Leu Gln Gln Ile Glu Glu Thr Gly
             340                 345                 350

Leu Thr Ile Glu Gln Val Lys Asp Ile Asn Arg Arg Met Ser Ile Gly
             355                 360                 365

Glu Ala Lys Ala Arg Arg Ala Lys Lys Glu Met Val Glu Ala Asn Leu
         370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                 405                 410                 415

Asp Lys Phe Glu Tyr Arg Arg Gly Tyr Lys Phe Ser Thr Tyr Ala Thr
             420                 425                 430
```

```
Trp Trp Ile Arg Gln Ala Ile Pro Arg Ser Ile Ala Asp Gln Ala Arg
            435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Val Glu Arg Met Leu Met Pro Glu Asp Lys Ile Arg Lys
                485                 490                 495

Val Leu Lys Ile Ala Lys Glu Pro Ser Met Glu Thr Pro Ile Gly
                500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
            595                 600                 605

Ser Phe Leu Asp Asp
        610

<210> SEQ ID NO 28
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 28

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175
```

-continued

Thr Ala Thr His Val Gly Ser Glu Leu Ser Gln Glu Asp Leu Asp Asp
                180                 185                 190

Asp Glu Asp Glu Asp Glu Glu Asp Gly Asp Asp Asp Ser Ala Asp Asp
            195                 200                 205

Asp Asn Ser Ile Asp Pro Glu Leu Ala Arg Glu Lys Phe Ala Glu Leu
        210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
        435                 440                 445

Thr Ile Arg Ile Pro Val His Met Ile Glu Asn Ile Asn Lys Leu Asn
450                 455                 460

Arg Ile Ser Arg Gln Met Leu Gln Glu Val Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Met Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg

-continued

<210> SEQ ID NO 29
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 29

```
Ser Phe Leu Asp Asp
            610

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
130                 135                 140

Leu Glu Gln Tyr Asp Arg Val Glu Ala Glu Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
```

```
            340                 345                 350
Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Pro Arg Ser Ile Ala Asp Gln Ala Arg
        435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Gly
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Asp Asp
    610

<210> SEQ ID NO 30
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 30

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
```

```
                   85                  90                  95
Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
            115                 120                 125

Gln Val Gln Cys Ser Val Ala Glu Tyr Pro Glu Ala Ile Thr Tyr Leu
            130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
                180                 185                 190

Asp Glu Asp Glu Asp Glu Glu Asp Gly Asp Asp Asp Ser Ala Asp Asp
            195                 200                 205

Asp Asn Ser Ile Asp Pro Glu Leu Ala Arg Glu Lys Phe Ala Glu Leu
            210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
            275                 280                 285

Lys Leu Cys Val Glu Gln Cys Lys Met Pro Lys Lys Asn Phe Ile Thr
            290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
            370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Pro Arg Ser Ile Ala Asp Gln Ala Arg
            435                 440                 445

Thr Ile Arg Ile Pro Val His Met Ile Glu Thr Ile Asn Lys Leu Asn
            450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510
```

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Pro Asp Tyr Thr Leu Glu Val
                565                 570                 575

Gly Lys Gln Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
            595                 600                 605

Ser Phe Leu Asp Asp
        610

<210> SEQ ID NO 31
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 31

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

```
Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Pro Arg Ser Ile Ala Asp Gln Ala Arg
        435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Arg Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Tyr Asp
    610

<210> SEQ ID NO 32
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 32
```

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
            115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Asp Gly Asp Asp Asp Ser Ala Asp Asp
    195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Ile Leu Lys Leu Ser Glu Val Phe
            245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
    275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415
```

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Pro Ala Ser
        435                 440                 445

Thr Ile Arg Ile Pro Val His Met Ile Glu Thr Ile Asn Lys Leu Asn
450                 455                 460

Arg Ser Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Pro Leu
        515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Val Asn Thr Asp Tyr Thr Leu Glu Glu Val
                565                 570                 575

Gly Lys Leu Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
        595                 600                 605

Ser Phe Leu Thr Asp
    610

<210> SEQ ID NO 33
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 33

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
            85                  90                  95

Pro Val Arg Met Tyr Met Arg Glu Met Gly Thr Val Glu Leu Leu Thr
        100                 105                 110

Arg Glu Gly Glu Ile Asp Ile Ala Lys Arg Ile Glu Asp Gly Ile Asn
    115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

```
Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
        435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Asn
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Arg Phe Asp Val Thr Arg Glu Arg Ile Arg Gln Ile Glu Ala
```

```
                580             585             590
Lys Ala Leu Arg Lys Leu Arg His Pro Ser Arg Ser Glu Val Leu Arg
            595             600             605

Ser Phe Leu Gly Asp
        610

<210> SEQ ID NO 34
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 34

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
```

```
                    325                 330                 335
Val His Arg Ala Leu Gln Lys Leu Gln Gln Ile Glu Glu Thr Gly
                340                 345                 350

Leu Thr Ile Glu Gln Val Lys Asp Ile Asn Arg Arg Met Ser Ile Gly
                355                 360                 365

Glu Ala Lys Ala Arg Arg Ala Lys Lys Glu Met Val Glu Ala Asn Leu
            370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Pro Arg Ser Ile Ala Asp Gln Ala Arg
                435                 440                 445

Thr Ile Arg Ile Pro Val His Met Ile Glu Thr Ile Asn Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
                500                 505                 510

Asp Asp Glu Asp Ser His Leu Gly Asp Phe Ile Glu Asp Thr Thr Leu
                515                 520                 525

Glu Leu Pro Leu Asp Ser Ala Thr Thr Glu Ser Leu Arg Ala Ala Thr
                530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Arg Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
                595                 600                 605

Ser Phe Leu Asp Asp
            610

<210> SEQ ID NO 35
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 35

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
        50                  55                  60

Leu Met Leu Ala Glu Asn Thr Ala Asp Glu Asp Ala Ala Glu Ala Ala
```

```
            65                  70                  75                  80
Ala Gln Val Leu Ser Ser Val Glu Ser Glu Ile Gly Arg Thr Thr Asp
                        85                  90                  95

Pro Val Arg Met Tyr Met Arg Glu Met Gly Thr Val Glu Leu Leu Thr
                        100                 105                 110

Arg Glu Gly Glu Ile Asp Ile Ala Lys Arg Ile Glu Asp Gly Ile Asn
                        115                 120                 125

Gln Val Gln Cys Ser Val Ala Glu Tyr Pro Glu Ala Ile Thr Tyr Leu
            130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Asp Leu Ala Pro
                        165                 170                 175

Thr Ala Thr His Val Gly Ser Glu Leu Ser Gln Glu Asp Leu Asp Asp
                        180                 185                 190

Asp Glu Asp Glu Asp Glu Asp Gly Asp Asp Asp Ser Ala Asp Asp
            195                 200                 205

Asp Asn Ser Ile Asp Pro Glu Leu Ala Arg Glu Lys Phe Ala Glu Leu
            210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                        245                 250                 255

Lys Gln Phe Arg Leu Val Pro Lys Gln Phe Asp Tyr Leu Val Asn Ser
                        260                 265                 270

Met Arg Val Met Met Asp Arg Val Arg Thr Gln Glu Arg Leu Ile Met
                        275                 280                 285

Lys Leu Cys Val Glu Gln Cys Lys Met Pro Lys Lys Asn Phe Ile Thr
            290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                        325                 330                 335

Val His Arg Ala Leu Gln Lys Leu Gln Gln Ile Glu Glu Thr Gly
                        340                 345                 350

Leu Thr Ile Glu Gln Val Lys Asp Ile Asn Arg Arg Met Ser Ile Gly
                        355                 360                 365

Glu Ala Lys Ala Arg Arg Ala Lys Lys Glu Met Val Glu Ala Asn Leu
            370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                        405                 410                 415

Asp Lys Phe Glu Tyr Arg Arg Gly Tyr Lys Phe Ser Thr Tyr Ala Thr
                        420                 425                 430

Trp Trp Ile Arg Gln Ala Ile Pro Arg Ser Ile Ala Asp Gln Ala Arg
                        435                 440                 445

Thr Ile Arg Ile Pro Val His Met Ile Glu Thr Ile Asn Lys Leu Asn
            450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                        485                 490                 495
```

```
Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
        530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
            595                 600                 605

Ser Phe Leu Gly Asp
            610

<210> SEQ ID NO 36
<211> LENGTH: 613
<212> TYPE: PRT
<213> ORGANISM: Artificial Sequence
<220> FEATURE:
<223> OTHER INFORMATION: Modified rpoD variant

<400> SEQUENCE: 36

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
        50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240
```

```
Ser His Ala Thr Ala Gln Glu Ile Leu Lys Leu Ser Glu Val Phe
            245                 250                 255

Lys Gln Phe Arg Leu Val Pro Lys Gln Phe Asp Tyr Leu Val Asn Ser
        260                 265                 270

Met Arg Val Met Met Asp Arg Val Arg Thr Gln Glu Arg Leu Ile Met
            275                 280                 285

Lys Leu Cys Val Glu Gln Cys Lys Met Pro Lys Lys Asn Phe Ile Thr
        290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
            325                 330                 335

Val His Arg Ala Leu Gln Lys Leu Gln Gln Ile Glu Glu Glu Thr Gly
        340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
            405                 410                 415

Asp Lys Phe Glu Tyr Arg Arg Gly Tyr Lys Phe Ser Thr Tyr Ala Thr
        420                 425                 430

Trp Trp Ile Arg Gln Ala Ile Thr Arg Ser Ile Ala Asp Gln Ala Arg
        435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Gly Pro Thr Pro
465                 470                 475                 480

Glu Glu Leu Val Glu Arg Met Leu Met Pro Glu Asp Lys Ile Arg Lys
            485                 490                 495

Val Leu Lys Ile Ala Lys Glu Pro Ile Ser Met Glu Met Pro Ile Gly
        500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
            565                 570                 575

Gly Lys Gln Phe Asp Val Thr Arg Glu Arg Ile Arg Gln Ile Glu Ala
        580                 585                 590

Lys Ala Leu Arg Lys Leu Arg His Pro Ser Arg Ser Glu Val Leu Arg
        595                 600                 605

Ser Phe Leu Asp Asp
    610
```

<210> SEQ ID NO 37
<211> LENGTH: 613
<212> TYPE: PRT
<213> ORGANISM: Artificial Sequence
<220> FEATURE:

<223> OTHER INFORMATION: Modified rpoD variant

<400> SEQUENCE: 37

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400
```

```
Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
        435                 440                 445

Thr Ile Arg Ile Pro Val His Met Ile Glu Asn Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Gly
                565                 570                 575

Gly Lys Gln Phe Asp Val Thr Arg Glu Arg Ile Arg Gln Ile Glu Ala
            580                 585                 590

Lys Ala Leu Arg Lys Leu Cys His Pro Ser Arg Ser Glu Val Leu Arg
        595                 600                 605

Ser Phe Leu Asp Asp
    610
```

MODIFIED RNA POLYMERASE SIGMA FACTOR 70 POLYPEPTIDE

CROSS-REFERENCES TO RELATED APPLICATIONS

This application is a U.S. national phase application of International PCT Patent Application No. PCT/KR2015/009381, which was filed on Sep. 4, 2015, which claims priority to Korean Patent Application Nos. 10-2015-0125440, filed Sep. 4, 2015 and 10-2014-0119138, filed Sep. 5, 2014 These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_047_00US_SeqList_ST25.txt. The text file is 166 KB, was created on Aug. 5, 2016, and is being submitted electronically via EFS-Web.

TECHNICAL FIELD

The present invention relates to a novel variant RNA polymerase sigma factor 70 ($\sigma^{70}$) polypeptide, a polynucleotide encoding the same, a microorganism containing the polypeptide, and a method for producing L-threonine by using the microorganism.

BACKGROUND ART

Generally, useful products such as amino acids can be produced by a fermentation method using microorganism strains developed via artificial mutation or genetic recombination. In particular, in developing microorganism strains for large-scale production of amino acids, it will be beneficial to discover genetic factors, which are directly/indirectly involved in a higher cascade step of the production, and appropriately utilize them to develop microorganism strains capable of producing higher yields. A representative technology in this regard may be global transcription machinery engineering (gTME), which can regulate the expression of all intracellular genes by causing random mutations on recruiting protein of RNA polymerase.

RNA polymerase is a macromolecule comprised of five subunits of $2\alpha$, $\beta$, $\beta'$, and $\omega$, and its holoenzymes are expressed as $\alpha_2\beta\beta'\omega$. Along with these holoenzymes, sigma ($\sigma$) factors, which are transcription initiation factors present in prokaryotes, can allow specific binding of RNA polymerase to promoters, and can be distinguished by their molecular weight. For example, $\sigma^{70}$ stands for a sigma factor having a molecular weight of 70 kDa (Gruber™, Gross C A, Annu Rev Microbiol. 57: 441-66, 2003).

Escherichia coli is known to possess a housekeeping sigma factor $\sigma^{70}$ (RpoD), a nitrogen-limitation sigma factor $\sigma^{54}$ (RpoN), a starvation/stationary phase sigma factor $\sigma^{38}$ (RpoS), a heat shock sigma factor $\sigma^{32}$ (RpoH), a flagellar sigma factor $\sigma^{28}$ (RpoF), an extracytoplasmic/extreme heat stress sigma factor $\sigma^{24}$ (RpoE), a ferric citrate sigma factor $\sigma^{19}$ (FecI), etc. These various sigma factors are known to be activated under different environmental conditions, and these characterized sigma factors can bind to the promoters of genes transcribed under specific environmental conditions, and thereby regulate the transcription of the genes. Studies on the increase of productivity of target materials by allowing random mutations on sigma factor 70 have been reported (Metabolic Engineering 9. 2007. 258-267), and there is also a study report on the enhanced tyrosine production using gTME technology in E. coli (U.S. Pat. No. 8,735,132).

DISCLOSURE

Technical Problem

The present inventors, while endeavoring to develop a microorganism capable of producing L-threonine at an improved concentration without growth retardation of a host cell, developed a novel modified sigma factor 70 polypeptide of RNA polymerase, and also discovered that a bacterial strain having an improved L-threonine-producing capability can be developed by introducing the novel modified sigma factor 70 polypeptide of RNA polymerase into Escherichia sp. having an L-threonine-producing capability.

Technical Solution

An object of the present invention is to provide a modified polypeptide having an activity of RNA polymerase sigma factor 70 of the amino acid sequence of SEQ ID NO: 8 wherein a part of the amino acid is substituted.

Another object of the present invention is to provide a polynucleotide encoding the polypeptide.

A further object of the present invention is to provide a transformed microorganism which includes the polypeptide.

A still further object of the present invention is to provide a method of producing L-threonine comprising culturing the microorganism; and recovering L-threonine from the cultured microorganism or a culture medium thereof.

Advantageous Effects

The present invention enables confirmation of a novel variant of a polypeptide of an RNA polymerase sigma factor 70 capable of upregulating the L-threonine-producing capability. Additionally, a microorganism capable of expressing the modified polypeptide based on the same has an excellent yield of L-threonine production, and thus the microorganism can provide convenience in production, and reduction in production cost from the industrial point of view.

BEST MODE

In an aspect of the above objects, the present invention provides a novel modified polypeptide having an activity of RNA polymerase sigma factor 70.

As used herein, the term "RNA polymerase sigma factor 70" refers to a protein $\sigma^{70}$, one of sigma factors and is called sigma factor D(RpoD). The protein $\sigma^{70}$ acts as one of transcription initiation factors along with RNA polymerase. Sigma factors are involved in the regulation of transcription by interacting with upstream DNA (UP element) on upstream of particular promoters and various transcription factors. In particular, sigma factor 70 ($\sigma^{70}$) is a major regulator among E. coli sigma factors, which controls most housekeeping genes and core genes, and is known to predominantly act during the exponential phase of E. coli (Jishage M, et al, J Bacteriol 178(18); 5447-51, 1996). The information on sigma factor 70 protein may be obtained from the known database such as NCBI GenBank, and, for example, it may be a protein with the Accession number NP 417539. Specifically, the σ⁷⁰ protein may include an amino acid sequence of SEQ ID NO: 8, but is not limited thereto, as long as the protein has the same activity as that of the σ⁷⁰ protein of the present invention.

As used herein, the term "modified polypeptide" generally refers to a wild-type polypeptide wherein a partial or entire amino acid sequence of the polypeptide is substituted. In the present invention, it refers to a polypeptide having the activity of sigma factor 70 (σ⁷⁰) of RNA polymerase with an amino acid sequence partially different from that of the wild-type, prepared by substituting part of the amino acid sequence of the wild-type sigma factor 70 (σ⁷⁰), i.e., a sigma factor 70 (σ⁷⁰)-modified polypeptide contributing to the enhancement of L-threonine-producing capability.

Specifically, the modified polypeptide may be a polypeptide having the activity of RNA polymerase sigma factor 70 of the amino acid sequence of SEQ ID NO: 8, wherein at least one amino acid at positions of 440 to 450; 459; 466; 470 to 479; 484; 495 to 499; 509; 527; 565 to 570; 575 to 580; 599; and 612, from the initial methionine as the first amino acid, is substituted with another amino acid. That is, the modified polypeptide may be a polypeptide wherein an amino acid in at least one of the 45 positions (positions 440 to 450, 459, 466, 470 to 479, 484, 495 to 499, 509, 527, 565 to 570, 575 to 580, 599, and 612) may be substituted with another amino acid. For example, the number of the position may be 1, 2, 3, 4, 5, 6, 7, 8, 9, 10, or more, but may not be limited thereto, as long as it has the activity of RNA polymerase sigma factor 70.

More specifically, the amino acid at position 440, 446, or 448 among those at positions 440 to 450; the amino acid at position 474 or 477 among those at positions 470 to 479; the amino acid at position 496 or 498 among those at positions 495 to 499; the amino acid at position 567 or 569 among those at positions 565 to 570; and the amino acid at position 576 or 579 among those at positions 575 to 580 may be substituted with another amino acid, but are not limited thereto.

Further more specifically, the amino acid at position 440 may be substituted with proline (T440P); the amino acid at position 446 with proline (Q446P); the amino acid at position 448 with serine (R448S); the amino acid at position 459 with asparagine (T459N); the amino acid at position 466 with serine (I466S); the amino acid at position 474 with valine (M474V); the amino acid at position 477 with glycine (E477G); the amino acid at position 484 with valine (A484V); the amino acid at position 496 with asparagine (K496N); the amino acid at position 498 with arginine (L498R); the amino acid at position 509 with methionine (T509M); the amino acid at position 527 with proline (T527P); the amino acid at position 567 with valine (M567V); the amino acid at position 569 with proline (T569P); the amino acid at position 576 with glycine (N576G); the amino acid at position 579 with arginine (Q579R), leucine (Q579L), threonine (Q579T), isoleucine (Q579I), glycine (Q579G), alanine (Q579A), proline (Q579P), or serine (Q579S); the amino acid at position 599 with cysteine (R599C); or the amino acid at position 612 with glycine (D612G), tyrosine (D612Y), threonine (D612T), asparagine (D612N), phenylalanine (D612F), lysine (D612K), serine (D612S), arginine (D612R), or histidine (D612H), or amino acid deletion with a stop codon (D612*), but may not be limited thereto. When the nucleotide is substituted with a stop codon there may be no amino acid.

Even more specifically, the modified polypeptide may be a polypeptide having an amino acid sequence among the SEQ ID NOS: 9 to 37, but may not be limited thereto.

The modified polypeptide of the present invention may include not only the amino acid sequences of SEQ ID NOS: 9 to 37, but also those having a homology of at least 70% with these sequences, specifically at least 80%, more specifically at least 90%, and even more specifically at least 99%, without limitation, as long as the protein can contribute to the enhancement of L-threonine-producing capability, compared to the wild-type sigma factor 70 (σ⁷⁰).

As a sequence having a homology as such, if the amino acid sequence is one which has substantially the same or corresponding biological activity of the modified sigma factor 70 (σ⁷⁰), it is obvious that amino acid sequences with a deletion, a modification, a substitution, or an addition in part of the sequences should also be included in the scope of the present invention.

As used herein, the term "homology" refers to a degree of identity of nucleotides or amino acid residues between two different amino acid sequences or nucleotide sequences of a gene encoding a protein, as aligning them to be maximally matched in a particular region. When there is a sufficiently high homology between them, the expression products of the corresponding gene may have the same or similar activities. The homology between sequences may be determined by a technology known in the art, for example, known sequence comparison programs including BLAST (NCBI), CLC Main Workbench (CLC bio), MegAlign (DNASTAR Inc), etc.

In another aspect, the present invention provides a polynucleotide encoding the modified polypeptide.

As used herein, the term "polynucleotide" refers to a polymer of nucleotides, in which nucleotide monomers are connected lengthwise in a chain shape by covalent bonds, specifically a DNA or RNA strand. More specifically, in the present invention, it may be a polynucleotide fragment encoding the modified polypeptide.

In an exemplary embodiment of the present invention, the gene encoding the amino acid sequence of RNA polymerase sigma factor 70 is rpoD gene, and may be specifically a gene derived from the genus *Escherichia*, and more specifically a gene derived from *E. coli*. The polynucleotide encoding the wild-type RNA polymerase sigma factor 70 may be represented by SEQ ID NO: 7, but is not limited thereto. Additionally, based on the genetic code degeneracy, polynucleotide sequences encoding the same amino acid sequence and variants thereof should also be included in the scope of the present invention.

Additionally, as for the modified polynucleotide of the present invention, based on the genetic code degeneracy, polynucleotide sequences encoding the same amino acid sequence and variants thereof should also be included in the scope of the present invention. Specifically, a nucleotide sequence encoding the polypeptide of the amino acid sequence of SEQ ID NO: 8, wherein at least one amino acid is substituted with another amino acid described above, or a variant thereof, may be included. In particular, the positions of the above variations may be the positions of amino acids at 440 to 450; 459; 466; 470 to 479; 484; 495 to 499; 509; 527; 565 to 570; 575 to 580; 599; and 612, from the initial methionine as the first amino acid.

More specifically, the positions of the above variations may be a substitution of the amino acid at position 440 with proline (T440P); a substitution of the amino acid at position 446 with proline (Q446P); a substitution of the amino acid at position 448 with serine (R448S); a substitution of the amino acid at position 459 with asparagine (T459N); a substitution of the amino acid at position 466 with serine (I466S); a substitution of the amino acid at position 474 with valine (M474V); a substitution of the amino acid at position 477 with glycine (E477G); a substitution of the amino acid at position 484 with valine (A484V); a substitution of the amino acid at position 496 with asparagine (K496N); a substitution of the amino acid at position 498 with arginine (L498R); a substitution of the amino acid at position 509 with methionine (T509M); a substitution of the amino acid at position 527 with proline (T527P); a substitution of the amino acid at position 567 with valine (M567V); a substitution of the amino acid at position 569 with proline (T569P); a substitution of the amino acid at position 576 with glycine (N576G); a substitution of the amino acid at position 579 with arginine (Q579R), leucine (Q579L), threonine (Q579T), isoleucine (Q579I), glycine (Q579G), alanine (Q579A), proline (Q579P), or serine (Q579S); a substitution of the amino acid at position 599 with cysteine (R599C); or a substitution of the amino acid at position 612 with glycine (D612G), tyrosine (D612Y), threonine (D612T), asparagine (D612N), phenylalanine (D612F), lysine (D612K), serine (D612S), arginine (D612R), or histidine (D612H); or a substitution of nucleotides with a stop codon (D612*), and a nucleotide sequence encoding the amino acid sequence of a modified polypeptide, wherein the amino acid substitution is a combination of at least one kind among the 34 amino acid substitutions described above, or a variant thereof, may be included.

Even more specifically, a nucleotide sequence encoding any amino acid sequence of the amino acid sequences of SEQ ID NOS: 9 to 37, or a variant thereof, may be included.

In another aspect, the present invention provides a host cell including the polynucleotide encoding the modified polypeptide, a microorganism transformed with a vector including the polynucleotide encoding the modified polypeptide, or a microorganism introduced with the modified polypeptide. Specifically, the introduction may be performed by transformation, but is not limited thereto.

Specifically, the microorganisms including the sigma factor 70 ($\sigma^{70}$)-modified polypeptide may have enhanced L-threonine-producing capability without growth inhibition of a host cell, compared to the microorganism including the wild-type sigma factor 70 ($\sigma^{70}$) polypeptide, and thus L-threonine can be obtained in high yield from these microorganisms.

As used herein, the term "vector" refers to any mediator for cloning and/or transfer of a nucleotide sequence into a host cell. The vector may be a replicon to which a different DNA fragment can bind, leading to replication of a combined fragment. As used herein, the term "replicon" refers to any genetic unit (e.g., plasmids, phages, cosmids, chromosomes, and viruses) which can be replicated by self-regulation. The vector may include viral- or non-viral mediators for in-vivo, ex-vivo, or in-vitro introduction of a nucleotide into a host cell, and may also include minicircle DNA. For example, the vector may include plasmids which do not have any bacterial DNA sequence (Ehrhardt, A. et al. (2003) HumGene Ther 10: 215-25; Yet, N. S. (2002) MoI Ther 5: 731-38; Chen, Z. Y. et al. (2004) Gene Ther 11: 856-64). Additionally, the vector may include transposons (*Annu Rev Genet.* 2003; 37: 3-29.), or artificial chromosomes. Specifically, pACYC177, pACYC184, pCL1920, pECCG117, pUC19, pBR322, pDZ, pCC1BAC, and pMW118 vectors may be used, but they are not limited thereto.

As used herein, the term "transformation" refers to introducing a gene into a host cell to be expressed in the host cell, and the transformed gene may not be particularly limited as long as it can be expressed in the host cell, regardless of whether the transformed gene is inserted into the chromosome of the host cell or positioned outside of the chromosome.

The gene may be introduced into a host cell in the form of an expression cassette, which is a polynucleotide construct including all essential elements for self-expression. The expression cassette may include a promoter, which is conventionally operably connected to the gene, a transcription termination signal, a ribosome-binding domain, and a translation termination signal. The expression cassette may be a self-replicable expression vector. Additionally, the gene may be one which is introduced into a host cell as a gene itself or in the form of a polynucleotide construct to be connected to a sequence necessary to be expressed in a host cell, but is not limited thereto.

As used herein, the term "host cell" or "microorganism" may refer to any cell or microorganism which includes a polynucleotide encoding a modified polypeptide, or which is transformed by a vector including the polynucleotide encoding a modified polypeptide and thus can express the modified polypeptide.

In the present invention, the host cell or microorganism may be any cell or microorganism capable of producing L-threonine and including the modified sigma factor 70 ($\sigma^{70}$). Examples of the microorganism may include *Escherichia* sp., *Serratia* sp., *Erwinia* sp., *Enterobacteria* sp., *Salmonella* sp., *Streptomyces* sp., *Pseudomona* sp., *Brevibacterium* sp., *Corynebacteria* sp., etc.; and specifically, a microorganism belonging to *Escherichia* sp., and more specifically, *Escherichia coli*, but it is not limited thereto.

In another aspect, the present invention provides a method of producing L-threonine including culturing the described microorganism in a medium, and recovering L-threonine from the cultured microorganism or the culture medium thereof.

As used herein, the term "culturing" refers to growing the microorganism in an appropriately and artificially adjusted environment. The culture process may be performed according to the appropriate medium and conditions for culture known in the art. The specific culturing process may be performed according to the general knowledge of one of ordinary skill in the art or the conventional method known in the art, and may be appropriately adjusted accordingly. Specifically, the culturing methods are described in detail in [*Chmiel; Bioprozesstechnik* 1. *Einfuhrung indie Bioverfahrenstechnik* (Gustav Fischer Verlag, Stuttgart, 1991), and *Storhas; Bioreaktoren and periphere Einrichtungen* (Vieweg Verlag, Braunschweig/Wiesbaden, 1994)]. Additionally, the culturing methods may include a batch culture, a continuous culture, and a fed-batch culture, and specifically, may be cultured continuously in a fed batch or repeated fed batch process, but are not limited thereto.

The culture medium used for cultivation should meet the requirements for each specific strain. Examples of the carbon source to be contained in the medium may include saccharides and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These carbon sources may be used alone or in combination, but are not limited thereto. Examples of the nitrogen source to be contained in the medium may include peptone, yeast extract, gravy, malt extract, corn steep liquor, and bean flour, urea or inorganic nitrogen sources such as ammonium sulfate, ammonium chloride, ammonium phosphate, ammonium carbonate, and ammonium nitrate. These nitrogen sources may be used alone or in combination, but are not limited thereto. Examples of the phosphorous source to be contained in the medium may include potassium dihydrogen phosphate, dipotassium hydrogen phosphate, and corresponding sodium-containing salts, but are not limited thereto. The culture media may include metals such as magnesium sulfate and iron sulfate. Additionally, materials essential for growth such as amino acids and vitamins may also be included. Additionally, precursors suitable for the medium may also be used. These materials may be added to the culture in the form of a batch culture or continuous culture, but are not limited thereto.

Additionally, the pH of the culture may be adjusted by adding a compound such as ammonium hydroxide, potassium hydroxide, ammonia, phosphoric acid, and sulfuric acid during cultivation in an appropriate manner. Additionally, bubble formation may be prevented during the cultivation using an antifoaming agent such as fatty acid polyglycol ester. Additionally, oxygen gas or an oxygen-containing gas may be added to a culture in order to maintain aerobic conditions in a culture liquid; no air may be added to maintain anaerobic conditions or microaerobic conditions; or nitrogen gas, hydrogen gas, or carbon dioxide may be injected. The cultivation may be performed at 27° C. to 37° C., and specifically at 30° C. to 35° C. The cultivation may be continued until the desired amount of production of a useful material can be obtained, and specifically for 10 hours to 100 hours. L-Threonine may be exported into a culture medium or may remain contained in the microorganism.

The method of recovering L-threonine from the microorganism or a culture thereof is widely known in the art. For example, methods such as filtration, anion exchange chromatography, crystallization, HPLC, etc. may be used, but are not limited thereto.

MODE FOR INVENTION

Hereinafter, the present invention will be described in more detail with reference to the following Examples. However, these Examples are for illustrative purposes only, and the invention is not intended to be limited by these Examples.

Example 1

Construction of a Recombinant Vector pCC1BAC-rpoD

In order to obtain a DNA fragment with a size of about 2.0 kb including the rpoD gene (NCBI Gene ID: 947567, SEQ ID NO: 7), the chromosomal DNA (gDNA) of *Escherichia coli* wild-type strain W3110 was extracted using Genomic-tip System (Qiagen), and a polymerase chain reaction ("PCR", hereinafter) was performed using the gDNA as a template with a PCR HL premix kit (BIONEER, Korea; the same product was used hereinafter).

A PCR reaction to amplify the rpoD gene was performed using primers SEQ ID NO: 1 and SEQ ID NO: 2 by denaturing at 95° C. for 30 seconds, annealing at 56° C. for 30 seconds, and elongation at 72° C. for 2 minutes for 27 cycles. The PCR products were digested with HindIII and EcoRI, electrophoresed on a 0.8% agarose gel, and a 2.0 kb DNA fragment ("rpoD fragment", hereinafter) was obtained therefrom by elution.

TABLE 1

| Primer No. | Nucleotide Sequence | SEQ ID NO |
|---|---|---|
| 1 | 5'-TACTCAAGCTTCGGCT TAAGTGCCGAAGAGC-3' | 1 |
| 2 | 5'-AGGGCGAATTCCTGAT CCGGCCTACCGATTA-3' | 2 |

Subsequently, the Copycontrol pCC1BAC vector (EPICENTRE, USA) was digested with HindIII and EcoRI, electrophoresed on a 0.8% agarose gel, and obtained therefrom by elution. The resultant was ligated to the rpoD fragment to construct the pCC1BAC-rpoD plasmid.

Example 2

Construction of a Recombinant Vector pCC1BAC-Partial rpoD

In order to obtain a DNA fragment with a size of about 1.5 kb including the region from the promoter to the BamHI restriction site within the rpoD gene of *E. coli* W3110, PCR was performed using the gDNA prepared in Example 1 as a template.

The PCR reaction was performed using primers SEQ ID NO: 1 and SEQ ID NO: 3 by denaturing at 95° C. for 30 seconds, annealing at 56° C. for 30 seconds, and elongation at 72° C. for 1 minute and 30 seconds for 27 cycles as in Example 1. The PCR products were digested with BamHI and HindIII, electrophoresed on a 0.8% agarose gel, and a 1.5 kb DNA fragment was obtained therefrom by elution.

TABLE 2

| Primer No. | Nucleotide Sequence | SEQ ID NO |
|---|---|---|
| 1 | 5'-TACTCAAGCTTCGGCT TAAGTGCCGAAGAGC-3' | 1 |
| 3 | 5'-GACGGATCCACCAGGT TGCGTA-3' | 3 |

Subsequently, the Copycontrol pCC1BAC vector was digested with BamHI and HindIII, electrophoresed on a 0.8% agarose gel, and obtained by elution. The resultant was ligated to the partial rpoD fragment to construct the pCC1BAC-patial rpoD plasmid.

Example 3

Generation of rpoD$^m$ Fragment Via Error-Prone PCR

In order to introduce a random modification in the conserved regions 2.4, 3, and 4 of the rpoD gene of W3110, the inventors intended to obtain a DNA pool of rpoD fragments, in which random modifications were introduced from the BamHI restriction site within the gene to the terminus encoding the gene.

To this end, a PCR reaction was performed using the gDNA obtained in Example 1 with a Diversify PCR Random Mutagenesis kit (catalog #: 630703; Clonetech), according to the conditions for mutagenesis reactions 4 in Table III described in the User Manual thereof. Specifically, the PCR was performed using the primers of SEQ ID NO: 2 and SEQ ID NO: 4, by denaturing at 94° C. for 30 seconds, annealing at 56° C. for 30 seconds, and elongation at 68° C. for 30 seconds for 25 cycles.

TABLE 3

| Primer No. | Nucleotide Sequence | SEQ ID NO |
|---|---|---|
| 2 | 5'-AGGGCGAATTCCTGAT CCGGCCTACCGATTA-3' | 2 |
| 4 | 5'-AACCTGGTGGATCCGT CAGGCGATC-3' | 4 |

Subsequently, the mutated art rpoD DNA pool, in which random nucleotide substitutions were introduced, was obtained as a PCR product, and the PCR product was digested with BamHI and EcoRI, electrophoresed on a 0.8% agarose gel, and a 0.5 kb DNA fragment ("art rpoD fragment", hereinafter) was obtained therefrom by elution.

Example 4

Construction of a Recombinant Vector pCC1BAC-rpoD Mutant Library Including Modified rpoD The pCC1BAC-partial rpoD vector constructed in Example 2 was treated with BamHI and EcoRI, and then treated with alkaline phosphatase (NEB).

Then, the art rpoD fragments obtained in Example 3 were treated with BamHI and EcoRI, respectively, and ligated to the pCC1BAC-partial rpoD vector, which was already treated with the restriction enzymes, transformed into TransforMax EPI300 Electrocompetent *E. coli* (EPICENTRE), cultured in an LB plate containing 15 μg/mL of chloramphenicol, and colonies were selected therefrom. The selected colonies were collected and subjected to a plasmid prep to construct a pCC1BAC-rpoD mutant library.

Example 5

Introduction of a pCC1BAC-rpoD Mutant Library into a Threonine-Producing Strain

The pCC1BAC-rpoD mutant library constructed in Example 4 was introduced into an electrocompetent cell of KCCM10541, which is a threonine-producing strain, by transformation.

In particular, the KCCM10541 (Korean Patent No. 10-0576342), the *E. coli* strain used in this Example, is an *E. coli* strain derived from the KFCC10718 (Korean Patent No. 10-0058286), in which galR gene is inactivated.

Example 6

Comparison of L-Threonine Producing Capabilities Between Recombinant Microorganisms and Confirmation of Nucleotide Sequences The recombinant microorganism library constructed in Example 5 was cultured in titer medium shown in Table 4 below, and the improvement in L-threonine production was examined.

TABLE 4

| Composition | Conc. (per 1 L) |
|---|---|
| Glucose | 70 g |
| KH$_2$PO$_4$ | 2 g |
| (NH$_4$)$_2$SO$_4$ | 25 g |
| MgSO$_4$•7H$_2$O | 1 g |
| FeSO$_4$•7H$_2$O | 5 mg |
| MnSO$_4$•4H$_2$O | 5 mg |
| DL-methionine | 0.15 g |
| Yeast extract | 2 g |
| Calcium carbonate | 30 g |
| pH | 6.8 |

Specifically, *E. coli* KCCM10541/pCC1BAC-rpoD and *E. coli* KCCM10541/pCC1BAC-rpoD mutant library, which were cultured overnight in a solid LB medium in a 33° C. incubator, were inoculated into 25 mL of titer medium by a platinum loop, respectively, and cultured in a 33° C. incubator while shaking at 200 rpm for 48 hours. The whole procedure was repeated to evaluate the rpoD mutant library, and those clones with improved yield were selected.

TABLE 5

| Strain | L-Threonine (g/L) | Increase rate of L-threonine Conc. (%) | Position of modification | SEQ ID NO |
|---|---|---|---|---|
| KCCM 10541 (parent strain) | 30.4 | — | | |
| KCCM 10541/pCC1BAC-rpoD | 30.4 | — | | 8 |
| KCCM 10541/pCC1BAC-rpoD$^{m1}$ | 32.8 | 7.9 | 579, 612 | 9 |
| KCCM 10541/pCC1BAC-rpoD$^{m2}$ | 33.0 | 8.6 | 579, 612 | 10 |
| KCCM 10541/pCC1BAC-rpoD$^{m3}$ | 33.6 | 10.5 | 579, 612 | 11 |
| KCCM 10541/pCC1BAC-rpoD$^{m4}$ | 34.0 | 11.8 | 579, 612 | 12 |
| KCCM 10541/pCC1BAC-rpoD$^{m5}$ | 33.4 | 9.9 | 579, 612 | 13 |
| KCCM 10541/pCC1BAC-rpoD$^{m6}$ | 34.0 | 11.8 | 579, 612 | 14 |
| KCCM 10541/pCC1BAC-rpoD$^{m7}$ | 33.5 | 10.2 | 579, 612 | 15 |
| KCCM 10541/pCC1BAC-rpoD$^{m8}$ | 32.5 | 6.9 | 579, 612 | 16 |
| KCCM 10541/pCC1BAC-rpoD$^{m9}$ | 32.0 | 5.3 | 579, 612 | 17 |

TABLE 5-continued

| Strain | L-Threonine (g/L) | Increase rate of L-threonine Conc. (%) | Position of modification | SEQ ID NO |
|---|---|---|---|---|
| KCCM 10541/pCC1BAC-rpoD$^{m10}$ | 32.0 | 5.3 | 579, 612 | 18 |
| KCCM 10541/pCC1BAC-rpoD$^{m11}$ | 32.1 | 5.6 | 579, 612 | 19 |
| KCCM 10541/pCC1BAC-rpoD$^{m12}$ | 32.0 | 5.3 | 579, 612 | 20 |
| KCCM 10541/pCC1BAC-rpoD$^{m13}$ | 34.0 | 11.8 | 579, 612 | 21 |
| KCCM 10541/pCC1BAC-rpoD$^{m14}$ | 34.2 | 12.6 | 440 | 22 |
| KCCM 10541/pCC1BAC-rpoD$^{m15}$ | 34.0 | 11.8 | 440, 496 | 23 |
| KCCM 10541/pCC1BAC-rpoD$^{m16}$ | 32.4 | 6.6 | 446, 448, 466, 527, 567 | 24 |
| KCCM 10541/pCC1BAC-rpoD$^{m17}$ | 32.5 | 7.1 | 440, 477, 498 | 25 |
| KCCM 10541/pCC1BAC-rpoD$^{m18}$ | 31.9 | 4.8 | 440, 599 | 26 |
| KCCM 10541/pCC1BAC-rpoD$^{m19}$ | 33.8 | 11.3 | 440, 484 | 27 |
| KCCM 10541/pCC1BAC-rpoD$^{m20}$ | 34.0 | 11.9 | 459, 474, 509 | 28 |
| KCCM 10541/pCC1BAC-rpoD$^{m21}$ | 31.9 | 4.8 | 440, 576 | 29 |
| KCCM 10541/pCC1BAC-rpoD$^{m22}$ | 33.9 | 11.6 | 440, 569 | 30 |

The result revealed, as shown in Table 5 above, that the parent strain KCCM 10541 and the control strain KCCM 10541/pCC1BAC-rpoD produced about 30.4 g/L of L-threonine when cultured for 48 hours.

In contrast, the recombinant *E. coli* introduced with the pCC1BAC-rpoD mutant library produced L-threonine ranging from 31.9 g/L to 34.2 g/L, thus showing an improved L-threonine-producing capability, compared to its parent strain, i.e., an improvement of 4.8% to 12.6% in L-threonine-producing capability compared to its parent strain.

Additionally, the position of modification and the substituted amino acid in each modification of modified rpoD gene of *E. coli* with improved L-threonine-producing capability were examined by sequencing, and the results are shown in Table 5.

Meanwhile, the recombinant *E. coli* with the most improvement in L-threonine-producing capability among the transformed *E. coli*, designated as "KCCM10541/pCC1BAC-rpoD$^{m19}$", was deposited on Aug. 6, 2014, at the Korean Culture Center of Microorganisms (Accession No: KCCM11560P).

Example 7

Construction of a Wild-Type Strain Introduced with Selected rpoD Variants and a Wild-Type Strain with Enhanced Biosynthesis Pathway for Threonine Production Thereto A few variations among the rpoD variants, which were confirmed with their improved threonine-producing capabilities in Example 6, were subjected to reconfirm their effects based on wild-type strains. The wild-type strain W3110 was transformed with the rpoD variations confirmed in Example 6 in the same manner as in Example 5, and was assigned as W3110/pCC1BAC-rpoD$^m$. The strain introduced with the rpoD variation was introduced with pACYC184-thrABC vector to provide the strain with a threonine-producing capability. The pACYC184-thrABC was constructed as described below.

PCR was performed using the genomic DNA of an L-threonine-producing *E. coli* strain KCCM 10541 (Korean Patent No. 10-0576342; Chinese Patent No. 100379851C) derived from *E. coli* strain KCCM 10718 (Korean Patent No. 10-0058286) as a template along with primers of SEQ ID NOS: 5 and 6 (Table 6). The DNA fragments obtained therefrom were separated/purified, prepared by treating with HindIII followed by purification, and thereby thrABC DNA fragments were prepared. The pACYC184 vector was prepared by treating with HindIII followed by purification, and ligated to thereby construct a pACYC184-thrABC vector. The thus-prepared vector was introduced into the W3110/pCC1BAC-rpoD$^m$ strain to construct a W3110/pCC1BAC-rpoD$^m$, pACYC184-thrABC strain.

TABLE 6

| SEQ ID NO | Primer Sequence |
|---|---|
| 5 | 5'-CGAGAAGCTTAGCTTTTCATTCTGACTGCA-3" |
| 6 | 5'-CGAGAAGCTTATTGAGATAATGAATAGATT-3' |

Example 8

Comparison of L-Threonine-Producing Capabilities Between a Wild-Type Strain, a Wild-Type Strain-Based Recombinant Microorganism with rpoD Variations, and the Strain with Enhanced Biosynthesis Pathway for Threonine Production Thereto The recombinant microorganisms prepared in Example 7 were cultured in an Erlenmeyer flask using a threonine titer medium, and its improved L-threonine productivity was thereby confirmed.

TABLE 7

| Composition | Conc. (per 1 L) |
|---|---|
| Glucose | 70 g |
| $KH_2PO_4$ | 2 g |
| $(NH_4)_2SO_4$ | 25 g |
| $MgSO_4 \cdot 7H_2O$ | 1 g |
| $FeSO_4 \cdot 7H_2O$ | 5 mg |
| $MnSO_4 \cdot 4H_2O$ | 5 mg |
| Yeast extract | 2 g |
| Calcium carbonate | 30 g |
| pH | 6.8 |

A platinum loop of each of the W3110/pCC1BAC-rpoD$^m$, W3110/pACYC184-thrABC, pCC1BAC, and W3110/pACYC184-thrABC, pCC1BAC-rpoD$^m$ strains cultured overnight in a solid LB medium in a 33° C. incubator was inoculated a titer medium (25 mL) shown in Table 7, and cultured in a 33° C. incubator at the rate of 200 rpm for 48 hours. The results are shown in Table 8 below.

TABLE 8

| Strain | OD | Glucose Consumption (g/L) | L-Threonine (g/L) | Yield (%) |
|---|---|---|---|---|
| W3110/pCC1BAC | 15.4 | 52.2 | 0 | 0 |
| W3110/pCC1BAC-rpoD | 15.4 | 52.2 | 0 | 0 |
| W3110/pCC1BAC-rpoD$^{m2}$ | 15.0 | 50.6 | 0 | 0 |
| W3110/pCC1BAC-rpoD$^{m19}$ | 15.5 | 52.0 | 0 | 0 |
| W3110/pACYC184-thrABC, pCC1BAC | 13.4 | 50.1 | 1.42 | 2.8 |
| W3110/pACYC184-thrABC, pCC1BAC-rpoD | 13.3 | 50.2 | 1.43 | 2.8 |
| W3110/pACYC184-thrABC, pCC1BAC-rpoD$^{m2}$ | 12.5 | 51.2 | 1.52 | 3.0 |
| W3110/pACYC184-thrABC, pCC1BAC-rpoD$^{m19}$ | 11.2 | 51.0 | 1.56 | 3.1 |

As shown in Table 8, the wild-type strain W3110/pCC1BAC and other strains of W3110/pCC1BAC-rpoD, W3110/pCC1BAC-rpoD$^{m2}$, and W3110/pCC1BAC-rpoD$^{m19}$ did not produce L-threonine at all when they were cultured for 48 hours, whereas the strains introduced with variants showed a decrease in glucose consumption. The W3110/pACYC184-thrABC, pCC1BAC strain, which is a recombinant strain constructed for producing L-threonine in a wild-type base, produced 1.42 g/L of L-threonine, and the W3110/pACYC184-thrABC, pCC1BAC-rpoD strain produced 1.43 g/L of L-threonine, thus showing a 2.8% yield. In contrast, the W3110/pACYC184-thrABC, pCC1BAC-rpoD$^{m2}$ strain and the W3110/pACYC184-thrABC, pCC1BAC-rpoD$^{m19}$ strain, which are wild-type-based recombinant strains introduced with the rpoD variations, respectively showed glucose consumption for 48 hours in the amount of 51.2 g/L and 51.0 g/L, and respectively produced threonine in the amount of 1.50 g/L and 1.53 g/L, thus showing 3.0% and 3.1% yields of threonine. That is, it was confirmed that the introduction of the rpoD variation improved the threonine yield by about 7% to 10%, thereby reconfirming that the rpoD variations selected in the present invention were valid variants.

Example 9

Examination of L-Threonine-Producing Capability by the Combination of Selected Recombinant rpoD Variations In order to examine the changes in threonine-producing capabilities by the combination of the variations included in each different subject among the selected variations, vectors with combined variations were constructed for several of the most frequently selected variations. An rpoD$^{m23}$ (SEQ ID NO: 31) variation, where the variations in amino acid sequences at positions of 440, 579, and 612 were combined, was constructed by combining the rpoD variation and the rpoD$^{m14}$ variation evaluated above. Further, an rpoD$^{m24}$ (SEQ ID NO: 32) variation, which was introduced with the most variations, was constructed by combining the rpoD$^{m16}$ variation and the rpoD$^{m3}$ variation. The rpoD$^{m24}$ variation was introduced with both the rpoD$^{m16}$ variation, which are variations in amino acid sequences at positions of 446, 448, 466, 527, and 567, and the rpoD$^{m3}$ variation in amino acid sequences at positions of 579 and 612. Additionally, among the 3 region variations, an rpoD$^{m25}$ (SEQ ID NO: 33) variation was constructed by combining the variation in the amino acid sequence at position 496 of the rpoD$^{m15}$ and the variations in the amino acid sequence at positions 579 and 612 of rpoD$^{m1}$.

Additionally, combinations of amino acid variations present in mutually different variations were constructed to confirm their effects. For example, the amino acid variations at the most frequently selected positions of 440, 579, and/or 612 were combined to construct the rpoD$^{m26}$ (SEQ ID NO: 34), where the variations at positions 440 and 579 were combined; and the rpoD$^{m27}$ (SEQ ID NO: 35), where the variations at positions 440 and 612 were combined.

Additionally, combinations of low-frequency variations among the selected variations were constructed to confirm their effects. For example, to construct the rpoD$^{m28}$ (SEQ ID NO: 36), the variation at position 477 of the rpoD$^{m17}$, the variation at position 484 of the rpoD$^{m19}$, and the variation at position 509 of the rpoD$^{m20}$ were combined; and to construct the rpoD$^{m29}$ (SEQ ID NO: 37), the variation at position 599 of the rpoD$^{m18}$, the variation at position 459 of the rpoD$^{m20}$, and the variation at position 576 of rpoD$^{m21}$ were combined.

The thus-prepared vectors introduced with rpoD$^{m23}$, rpoD$^{m24}$, rpoD$^{m25}$, rpoD$^{m26}$, rpoD$^{m27}$, rpoD$^{m28}$, and rpoD$^{m29}$ variations were introduced into W3110 along with the pACYC184-thrABC vector prepared in Example 7, and titer evaluation was performed using the medium shown in Table 7. The results are shown in Table 9 below.

TABLE 9

| Strain | OD | Glucose Consumption (g/L) | L-Threonine (g/L) | Yield (%) | Position of Variation | SEQ ID NO |
|---|---|---|---|---|---|---|
| W3110/pACYC184-thrABC, pCC1BAC | 13.2 | 50.5 | 1.40 | 2.8 | | |
| W3110/pACYC184-thrABC, pCC1BAC-rpoD | 13.1 | 50.8 | 1.44 | 2.8 | | |
| W3110/pACYC184-thrABC, pCC1BAC-rpoD$^{m23}$ | 13.6 | 52.5 | 1.61 | 3.1 | 440, 579, 612 | 31 |
| W3110/pACYC184-thrABC, pCC1BAC-rpoD$^{m24}$ | 12.0 | 49.5 | 1.50 | 3.0 | 446, 448, 466, 527, 567, 579, 612 | 32 |
| W3110/pACYC184-thrABC, pCC1BAC-rpoD$^{m25}$ | 12.9 | 52.5 | 1.52 | 2.9 | 496, 579, 612 | 33 |
| W3110/pACYC184-thrABC, pCC1BAC-rpoD$^{m26}$ | 13.3 | 51.4 | 1.52 | 3.0 | 440, 579 | 34 |
| W3110/pACYC184-thrABC, pCC1BAC-rpoD$^{m27}$ | 13.9 | 50.5 | 1.54 | 3.0 | 440, 612 | 35 |
| W3110/pACYC184-thrABC, pCC1BAC-rpoD$^{m28}$ | 12.8 | 48.5 | 1.39 | 2.9 | 477, 484, 509 | 36 |
| W3110/pACYC184-thrABC, pCC1BAC-rpoD$^{m29}$ | 12.6 | 50.3 | 1.49 | 3.0 | 459, 576, 599 | 37 |

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A modified RNA polymerase sigma factor 70 polypeptide, wherein the modified polypeptide has RNA polymerase sigma factor 70 activity, wherein the modified polypeptide comprises an amino acid sequence that has at least 90% sequence identity to the amino acid sequence of SEQ ID NO: 8, wherein an amino acid corresponding to position 612 of the amino acid sequence of SEQ ID NO: 8 is substituted with tyrosine, threonine, asparagine, lysine, serine, arginine, or histidine in the amino acid sequence of the modified polypeptide;
   wherein the modified polypeptide is able to increase L-threonine production in a microorganism comprising the modified polypeptide; and
   wherein the modified polypeptide further comprises one to six mutation(s) of an amino acid corresponding to positions selected from 440, 446, 448, 459, 466, 474, 477, 484, 496, 498, 509, 527, 567, 569, 576, 579, and 599 of the amino acid sequence of SEQ ID NO: 8.

2. The modified polypeptide of claim 1,
   wherein the amino acid corresponding to position 440 of SEQ ID NO: 8 is substituted with proline in the amino acid sequence of the modified polypeptide;
   wherein the amino acid corresponding to position 446 of SEQ ID NO: 8 is substituted with proline in the amino acid sequence of the modified polypeptide;
   the amino acid corresponding to position 448 of SEQ ID NO: 8 is substituted with serine in the amino acid sequence of the modified polypeptide;
   the amino acid corresponding to position 459 of SEQ ID NO: 8 is substituted with asparagine in the amino acid sequence of the modified polypeptide;
   the amino acid corresponding to position 466 of SEQ ID NO: 8 is substituted with serine in the amino acid sequence of the modified polypeptide;
   the amino acid corresponding to position 474 of SEQ ID NO: 8 is substituted with valine in the amino acid sequence of the modified polypeptide;
   the amino acid corresponding to position 477 of SEQ ID NO: 8 is substituted with glycine in the amino acid sequence of the modified polypeptide;
   the amino acid corresponding to position 484 of SEQ ID NO: 8 is substituted with valine in the amino acid sequence of the modified polypeptide;
   the amino acid corresponding to position 496 of SEQ ID NO: 8 is substituted with asparagine in the amino acid sequence of the modified polypeptide;
   the amino acid corresponding to position 498 of SEQ ID NO: 8 is substituted with arginine in the amino acid sequence of the modified polypeptide;
   the amino acid corresponding to position 509 of SEQ ID NO: 8 is substituted with methionine in the amino acid sequence of the modified polypeptide;
   the amino acid corresponding to position 527 of SEQ ID NO: 8 is substituted with proline in the amino acid sequence of the modified polypeptide;
   the amino acid corresponding to position 567 of SEQ ID NO: 8 is substituted with valine in the amino acid sequence of the modified polypeptide;

the amino acid corresponding to position 569 of SEQ ID NO: 8 is substituted with proline in the amino acid sequence of the modified polypeptide;

the amino acid corresponding to position 576 of SEQ ID NO: 8 is substituted with glycine in the amino acid sequence of the modified polypeptide;

the amino acid corresponding to position 579 of SEQ ID NO: 8 is substituted with alanine, arginine, leucine, threonine, isoleucine, glycine, proline, or serine in the amino acid sequence of the modified polypeptide; or the amino acid corresponding to position 599 of SEQ ID NO: 8 is substituted with cysteine in the amino acid sequence of the modified polypeptide.

3. A method for producing L-threonine comprising culturing a microorganism comprising the modified polypeptide of claim 1 in a medium to produce L-threonine; and recovering the L-threonine from the cultured microorganism or the culture medium.

4. A method for producing L-threonine comprising culturing a microorganism comprising the modified polypeptide of claim 2 in a medium to produce L-threonine; and recovering the L-threonine from the cultured microorganism or the culture medium.

5. The method for producing L-threonine of claim 3, wherein the microorganism is *Escherichia coli*.

6. A modified RNA polymerase sigma factor 70 polypeptide wherein the modified polypeptide comprises an amino acid sequence selected from the group consisting of SEQ ID NO: 9 to 21, 32, and 33.

7. A polynucleotide encoding the modified polypeptide of claim 1.

8. A microorganism comprising the modified polypeptide of claim 1.

9. The microorganism of claim 8, wherein the microorganism is *Escherichia coli*.

* * * * *